(12) United States Patent
O'Neil et al.

(10) Patent No.: US 9,314,231 B2
(45) Date of Patent: Apr. 19, 2016

(54) USE OF AN EXPANDABLE STENT AS AN IMPLANT CONDUIT IN THE LATERAL APPROACH TO THE SPINE

(71) Applicants: Michael J O'Neil, West Barnstable, MA (US); Thomas M DiMauro, Southboro, MA (US)

(72) Inventors: Michael J O'Neil, West Barnstable, MA (US); Thomas M DiMauro, Southboro, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 204 days.

(21) Appl. No.: 13/887,838

(22) Filed: May 6, 2013

(65) Prior Publication Data
US 2014/0330083 A1    Nov. 6, 2014

(51) Int. Cl.
*A61B 17/02* (2006.01)
*A61B 5/00* (2006.01)
*A61B 17/34* (2006.01)
*A61B 17/00* (2006.01)

(52) U.S. Cl.
CPC ............. *A61B 17/02* (2013.01); *A61B 17/3439* (2013.01); *A61B 5/4041* (2013.01); *A61B 5/4893* (2013.01); *A61B 2017/00261* (2013.01); *A61B 2017/00867* (2013.01); *A61B 2017/3488* (2013.01)

(58) Field of Classification Search
CPC ............. A61B 17/02; A61B 5/00; A61B 5/40; A61B 17/3439
USPC ............ 600/202, 235, 546, 547, 554; 606/32, 606/41
See application file for complete search history.

(56) References Cited

U.S. PATENT DOCUMENTS

| | | | |
|---|---|---|---|
| 4,545,374 A | 10/1985 | Jacobson | |
| 5,460,170 A | 10/1995 | Hammerslag | |
| 6,104,960 A * | 8/2000 | Duysens et al. | ............. 607/117 |
| 6,371,968 B1 | 4/2002 | Kogasaka et al. | |
| 7,962,191 B2 | 6/2011 | Marino et al. | |
| 8,000,782 B2 | 8/2011 | Gharib et al. | |
| 8,027,716 B2 | 9/2011 | Gharib et al. | |
| 8,372,131 B2 | 2/2013 | Hestad et al. | |
| 2007/0232864 A1 * | 10/2007 | Sharp et al. | ............. 600/227 |
| 2008/0065144 A1 * | 3/2008 | Marino et al. | ............. 606/198 |
| 2009/0024203 A1 * | 1/2009 | Hestad et al. | ............. 623/1.15 |
| 2010/0049003 A1 | 2/2010 | Levy | |
| 2010/0076335 A1 * | 3/2010 | Gharib et al. | ............. 600/546 |
| 2010/0286784 A1 * | 11/2010 | Curran et al. | ............. 623/17.16 |
| 2012/0232552 A1 | 9/2012 | Morgenstern et al. | |

FOREIGN PATENT DOCUMENTS

WO    WO 2010/114625 A2    10/2010

OTHER PUBLICATIONS

European Search Report, Application No. PCT/US2014/035613, dated Nov. 10, 2014, 7 pages.
Davis, J Bone Joint Surg. Am. Aug. 17, 2011; 93(16): 1482-7.
Written Opinion of the International Searching Authority, Application No. PCT/US2014/035613, date of Report Nov. 10, 2015, 8 pages.

* cited by examiner

*Primary Examiner* — Christopher Beccia
(74) *Attorney, Agent, or Firm* — Raymond N. Scott, Jr.

(57) ABSTRACT

The use of a memory metal mesh stent as a retractor in a lateral approach to the spine. The expanded stent is used as a conduit through which an implant can pass. This advance is predicated upon the appreciation that modern stent implants have diameters that are large enough to accommodate passage of an intervertebral spinal implant therethrough.

36 Claims, 7 Drawing Sheets

FIG. 1A
FIG. 1B
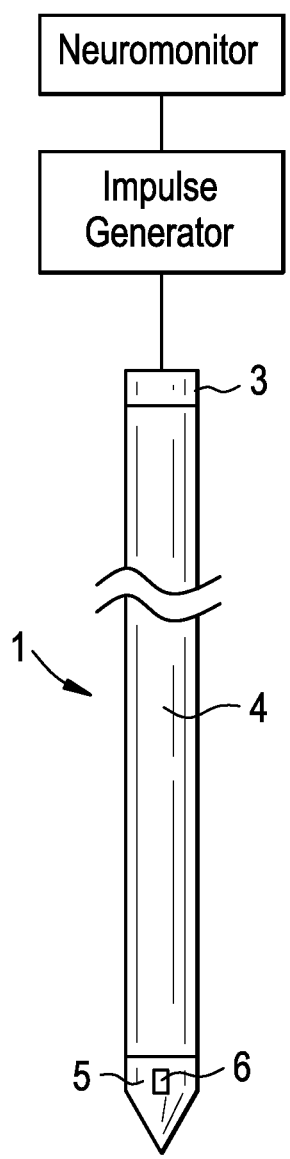
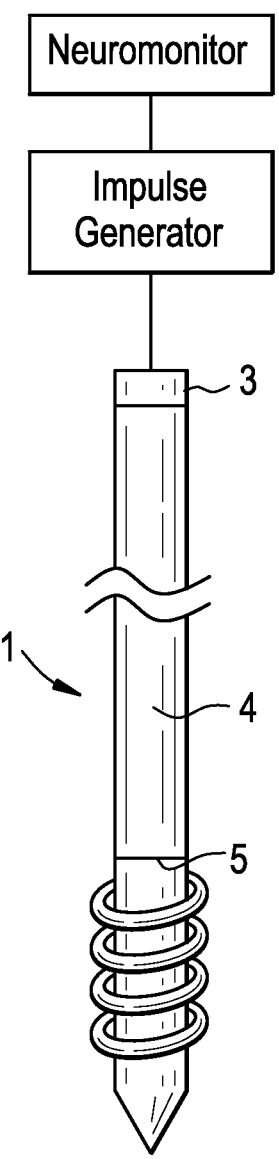

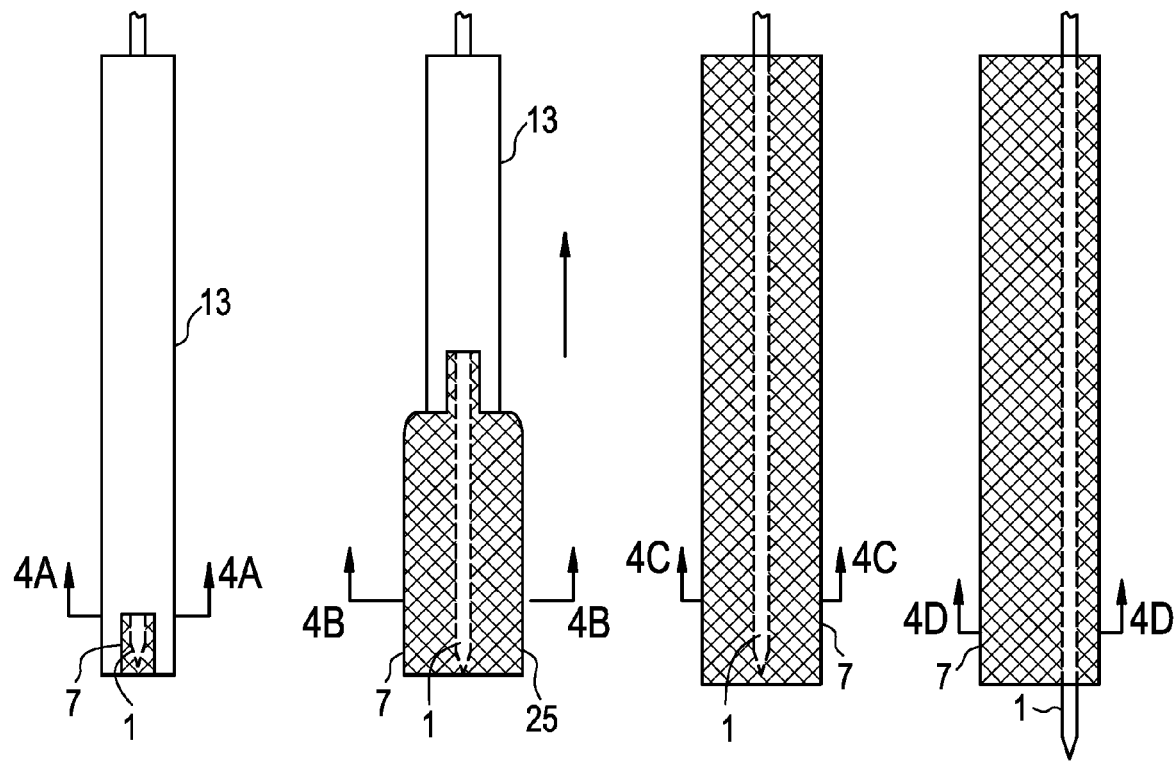
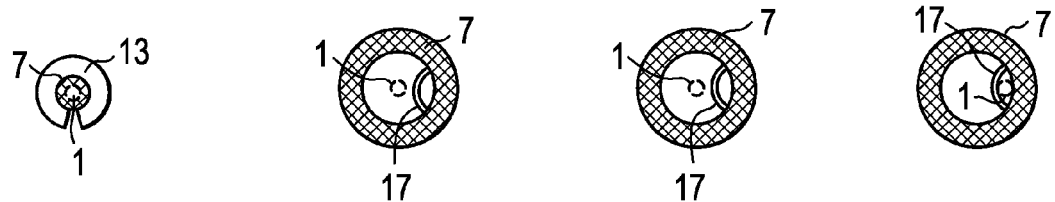

USE OF AN EXPANDABLE STENT AS AN IMPLANT CONDUIT IN THE LATERAL APPROACH TO THE SPINE

BACKGROUND OF THE INVENTION

The lateral access approach is frequently utilized to deliver interbody fusion cages to the lumbar spine. In comparison to conventional anterior or posterior approaches to the lumbar spine, the lateral approach is thought to minimize posterior and/or anterior tissue damage as well as reduce surgery time, associated blood loss, vascular damage and infection risk.

When the lateral access approach is utilized, the surgeon may use sequential dilation followed by tissue retraction in order to provide a minimally invasive path to the disc space. In addition, neuromonitoring is typically undertaken in order to avoid disturbing nerves residing in the lumbar plexus. In particular, one of the cannulae used in the sequential dilation or the retractor used for retraction may be fitted with an electrode capable of detecting a proximate nerve.

Despite these efforts, there still appears to be a significant incidence of neural deficit associated with the lateral approach to the spine. For example, there appears to be about a 30-35% incidence of transient but severe leg pain in patients undergoing an L4-L5 intervertebral fusion by a lateral approach.

Because of the proximity of the neural elements, in particular the femoral nerve, to the center of the disc space, the transpsoas lateral surgical approach to the L4-L5 disc space will likely cause intraoperative displacement of neural structures from their anatomic course during retractor dilation. Careful attention should be paid to retractor placement and dilation time during transpsoas lateral access surgery, particularly at the L4-L5 disc. Davis, *J Bone Joint Surg Am.* 2011 Aug. 17; 93(16):1482-7.

U.S. Pat. No. 5,460,170 (Hammerslag) teaches a self-retaining surgical mesh retractor suitable for use in small surgical incisions or punctures, able to expand the incision or puncture to one or more enlarged cross-sectional areas and designed to protect the edges of the incision or puncture. The surgical retractor comprises a radially expandable tubular body having a control at the proximal end. Pull wires couple the control to the tubular body such that force applied to the control is transmitted to the tubular body as axially compressive force.

U.S. Pat. No. 8,372,131 (Hestad) teaches an expandable surgical site access system and method for using the expandable surgical site access system to perform minimally invasive, percutaneous surgeries to access the spine or other bone structures, organs, or locations of the body is disclosed. In one embodiment, the surgical site access system includes an elongated, expandable mesh stent that is particularly adapted to be deployed in a body during a surgical procedure to provide access to a surgical site within the body. The stent defines a working channel through the body from a point of entry to the surgical site.

U.S. Pat. No. 7,962,191 (Marino) teaches an expandable tip cannula system, comprising: a hollow cannula shaft having a proximal end and a distal end; and an expandable tip mounted at the distal end of the hollow cannula shaft, the expandable tip comprising a plurality of generally-triangular shaped petals held together in a radially-inwardly tapered arrangement between adjacent petals, each petal comprising a nerve sensing electrode disposed therein. Marino further teaches using an expandable mesh stent to push away nerves.

WO 2010-114625 (Hardenbrook) discloses a retractor system comprising two retractors.

U.S. Pat. No. 8,000,782 (Gharib I) and U.S. Pat. No. 8,027,716 (Gharib II) disclose systems and related methods for performing surgical procedures and assessments, including the use of neurophysiology-based monitoring to: (a) determine nerve proximity and nerve direction to surgical instruments employed in accessing a surgical target site; (b) assess the pathology (health or status) of a nerve or nerve root before, during, or after a surgical procedure; and/or (c) assess pedicle integrity before, during or after pedicle screw placement, all in an automated, easy to use, and easy to interpret fashion so as to provide a surgeon-driven system.

SUMMARY OF THE INVENTION

The present inventors have developed inventions related to using an expandable stent as a retractor and conduit in a lateral approach to the spine, preferably without a preceding step of sequential dilation. Preferably, the stent is made of memory mesh, more preferably memory metal mesh.

In one aspect of the present invention, the expanded stent is used as a conduit through which an implant can pass. This is an advance over the Marino technology, which merely used its stent as a dilator and then removed the stent before introduction of the implant. This advance is predicated upon the appreciation that modern stent implants (which have expanded diameters up to 25-30 mm) are large enough to accommodate passage of an intervertebral spinal implant therethrough and yet sturdy enough to retain an opening in a psoas muscle in a retracted state. Moreover, since the unexpanded stents have inner diameters in the range of about 1-2 mm, they can be slid directly over an electrified 1-2 mm probe in their unexpanded state, thereby obviating the need to use sequential dilation.

Therefore, in accordance with the present invention, there is provided a method of inserting an implant, comprising the steps of:
a) advancing an expandable stent in its unexpanded condition to an intervertebral target;
b) expanding the stent to its expanded condition to provide a conduit;
c) passing a spinal implant through the conduit;
d) implanting the spinal implant in the intervertebral target.

When a direct lateral approach to the spine is undertaken so that the approach travels through the psoas muscle, it is desirable to perform neuromonitoring within the psoas in order to detect and avoid the nerves of the lumbar plexus that reside in the psoas muscle. In these cases, the method of the present invention further comprises advancing an electrified probe 1 (FIG. 1A or FIG. 1B) through the psoas and up to a target intervertebral disc prior to advancing the stent to the spine. (Alternatively, the probe and stent can be advanced together as an assembly). The electrified probe is typically made of an electrically conductive metal that is coated with a resistive coating, save its proximal 3 and distal 5 ends, as in FIG. 1B. The bare portion at the proximal end of the probe is connected to an impulse generator, which is in turn connected to a neuromonitoring system. Impulses are sent through the probe, out the bare distal end of the probe, and into the psoas in order to detect the presence of nerves of the lumbar plexus. Alternatively, a portion 6 of the probe distal end portion (i.e., an island) may also be selectively bare, as in FIG. 1A. Once the probe has identified a safe region, the expandable stent 7 may be advanced to the safe region by sliding it over the electrified probe, so that the outer surface of the probe 9 contacts the inner surface 11 of the unexpanded stent (FIGS. 2A and 2B). During this advance of the stent, the stent may be held in its unexpanded condition by a constraining sheath 13 surrounding the stent. Once the stent arrives at its destination in the psoas, expansion of the stent may then be easily accomplished by simply removing the sheath from the stent (FIGS. 2C and 2D). Thereafter, the probe may attach to the stent so as to provide an anchor (FIG. 2E). Lastly, discectomy instruments and then the implant 15 may be passed through the stent (FIG. 2F).

Likewise, and now referring to FIGS. 3A-3D, in some embodiments, the stent 7 and sheath 13 slid over the probe 1 (FIG. 3A). The sheath is then removed (FIGS. 3B and 3C). The probe is then attached to the stent to serve as an anchor (FIG. 3D).

FIGS. 4A-4D represent transverse cross-sectional views of FIGS. 3A-3D, and further show the receiver 17 located on the stent for securing the probe thereto.

In other embodiments, as in FIG. 5, a balloon 21 may be used to expand the stent. In such as case, an assembly comprising an inner catheter 23, and intermediate balloon 21, and an outer unexpanded stent 7 may be selected. In preferred embodiments of this aspect, neuromonitoring of the psoas is first performed with the probe to identify a safe region. Next, the inner catheter component of the assembly is then slid over the probe 1. The balloon is then expanded to expand the stent. The balloon is then deflated and removed, thereby leaving an expanded stent within the psoas.

Preferably, the expansion of the stent produces a conduit having a diameter of between 8 mm and 25 mm, preferably between 15 mm and 25 mm. In this condition, the expanded stent can accommodate the passage of conventional lateral fusion devices (such as CONCORDE LS cage from DePuy Synthes Spine).

DESCRIPTION OF THE FIGURES

FIGS. 1A-1B are probes of the present invention attached to impulse generators and neuromonitors.

FIGS. 3A-3D disclose side views of using the assembly of the present invention.

FIGS. 4A-4D disclose cross-sections of FIGS. 3A-3D.

DETAILED DESCRIPTION OF THE INVENTION

Figure 2A:
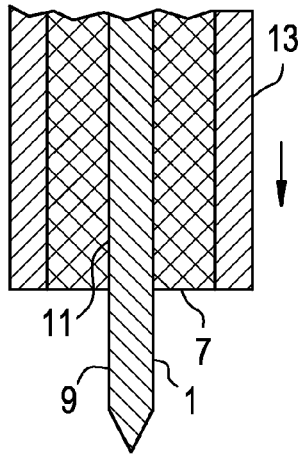
FIGS. 2A-2F disclose cross-sectional views of using the assembly of the present invention.
Figure 2B:
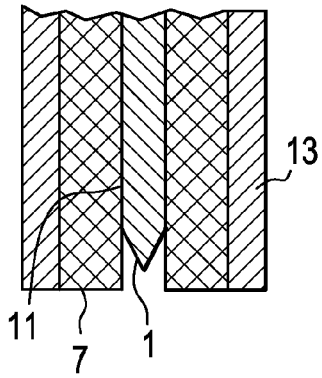
Figure 2C:
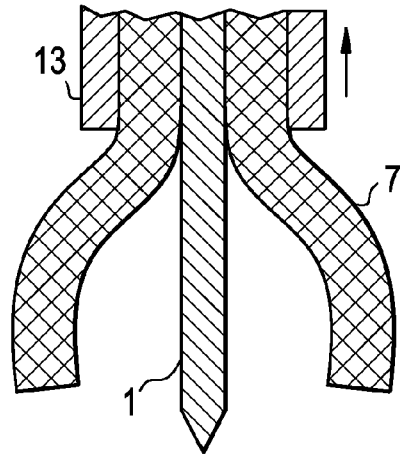
Figure 2D:
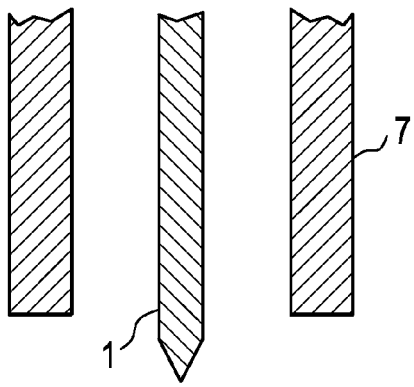
Figure 2E:
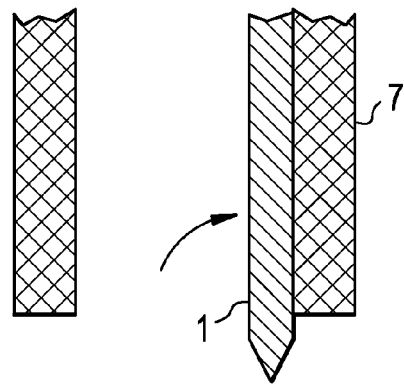
Figure 2F:
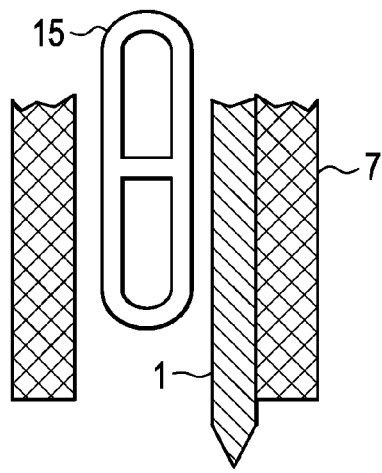
Figure 5:
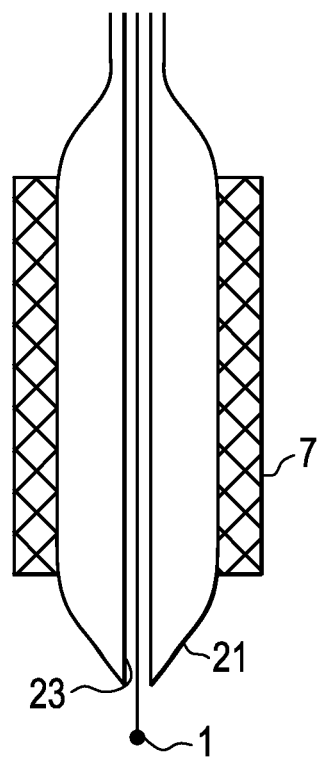
FIG. 5 discloses an embodiment comprising a balloon-expandable stent.
Figure 6:
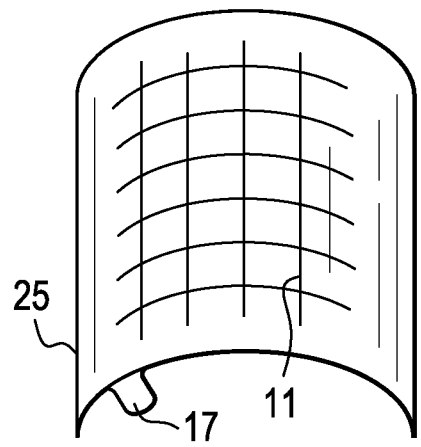
FIG. 6 is a section of a stent having a receiver at its distal end portion.

It is a primary intention of the present invention to use the stent as a conduit through which an implant or an instruments may pass as they proceed to the spine. Accordingly, it would be useful to be able to dock the stent upon the patient's spine, so as to provide locational stability to the stent as it carries out its conduit function. In such a case, the distal end portion (25 in FIG. 3B) of the stent may be fitted with a receiver 17 (such as a loop) that extends inward from the inner surface 11 of the stent and is adapted to receive an anchoring component. See FIG. 6. An anchoring component (such as a threaded element) can pass distally through the receiver and into the patient's spine, thereby anchoring the expanded stent to the spine and providing the desired locational stability.

In some embodiments, the anchoring component passes into a vertebral body of the patient. In other embodiments, the anchoring component passes into the annulus fibrosus of the target disc.

Figure 7A:
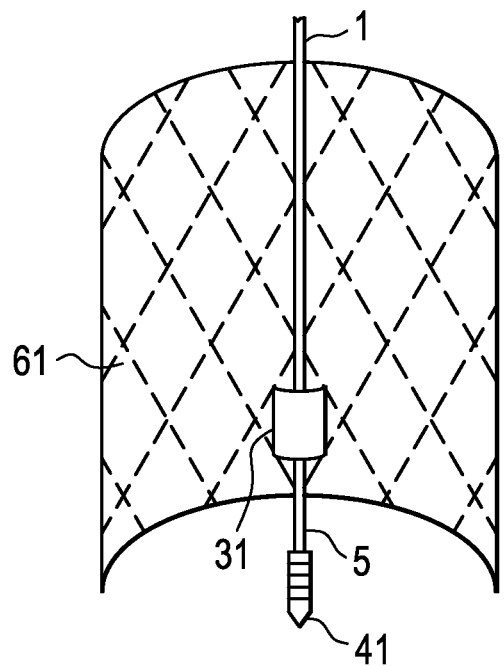
FIGS. 7A-7B disclose portions of a stent having a receiver attached thereto.
Figure 7B:
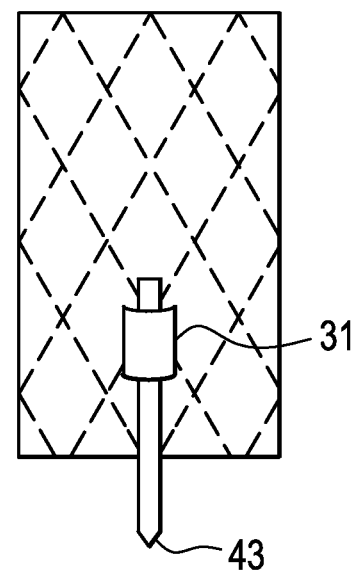

In some embodiments, the anchoring component is a screw. A screw can be easily threaded into the patient's spine and easily removed therefrom. In some embodiments, the anchoring component is a shim having a blade. In some embodiments, the probe used for neuromonitoring also functions as the anchoring component. In one embodiment thereof, the distal end portion 5 of the probe 1 comprises a thread 41 (FIG. 7A). In another embodiment thereof, the distal end portion of the probe comprises a tip 43 adapted to pierce bone (FIG. 7B). When the probe is used as the anchor, it need not be removed from the expanded stent.

In some embodiments, the receiver extends inward from the inner surface of the stent. In some embodiments, the receiver extends outward from the outer surface of the stent.

Now referring to FIGS. 7A and 7B, in some embodiments, the receiver may be formed as a sleeve 31 on a fabric supported by the mesh. In some embodiments thereof, the stent is a stent graft comprising a mesh stent having a fabric on its surface (preferably, its inside surface), and the sleeve is attached to or formed on the inner surface of the fabric. For the purposes of the present invention, a fabric includes a woven material, a cloth, a polymeric material, a coating such as polyurethane, silicones, teflons, and elastomers. In some embodiments, the sleeve comprises an elastomer. The elasticity of this sleeve allows the anchor to be held snugly between the sleeve and the annular fabric. The fabric also provides the benefit of preventing tissue ingress of the psoas into the expanded stent bore. Another benefit of the fabric may lie in its adding to the ease of extraction of the stent.

In some embodiments in which the stent is unexpanded (FIG. 8), the sleeve 31 occupies substantially all of the inner bore in the distal portion of the unexpanded stent 7. In this condition, the probe is necessarily received in the sleeve when the stent is slid over the probe. When the stent becomes expanded, the probe moves preferentially to the inner edge of the stent along with the sleeve. In some embodiments, the sleeve overlaps substantially the entire distal edge of the inner diameter of the unexpanded stent, thereby requiring the probe to enter the sleeve as the stent is slid over the probe.

Figure 12:
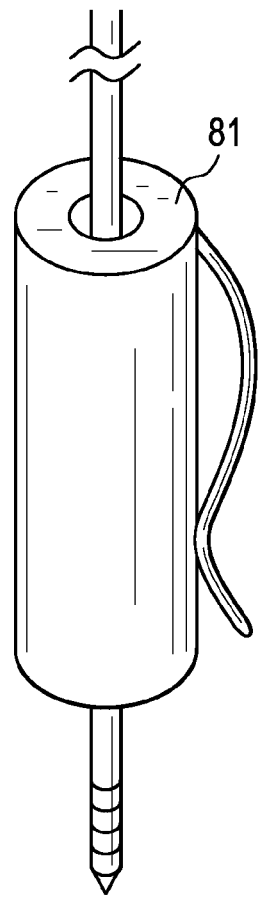
FIG. 12 is a receiver of the present invention.

In some embodiments, the receiver is integral with the mesh. In some embodiments (FIG. 12), the receiver 81 may be removable from the mesh.

The probe is generally an elongated element formed of an electrically conductive material. In some embodiments (as in FIGS. 1A and 1B), a proximal portion 3 of the probe is attached to an electrical impulse generator (which may be part of a neuromonitoring system). In some embodiments, an intermediate portion 4 of the probe is coated with an electrical insulator. In preferred embodiments, the distal end portion 5 of the probe is uncoated, so as to provide the probe with an ability to neuromonitor oncoming tissue during its advance. Alternatively, only an island 6 on the distal end portion of the probe may be bare.

Typically, the stent of the present invention has an elongated annular shape. It should be at least about 20 to 50 mm long in order to traverse the breadth of a typical psoas muscle.

In some embodiments, the stent in its unexpanded condition has an inner diameter of about 1-2 mm. These small diameters enable the unexpanded stent to slide over the typical 1-2 mm electrified probe. In some embodiments, the stent in its expanded condition has an inner diameter of about 8 mm to 25 mm, thereby enabling passage of fusion cages and instruments.

In some embodiments, the stent is made of a biocompatible material, preferably a metal (such as CoCr or stainless steel) or a polymer. In preferred embodiments, the stent is made of a memory metal, such as nitinol. Preferably, the stent has a mesh pattern.

Figure 9:
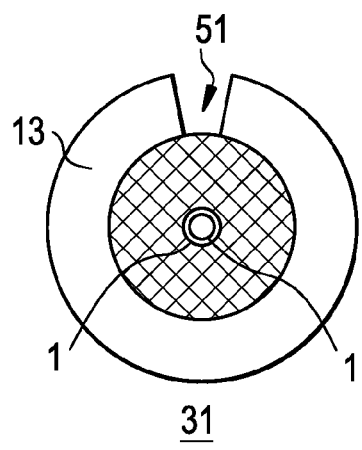
FIG. 9 discloses a transverse cross-section of a directional electrode embodiment of the assembly.

As discussed above, in preferred embodiments of the present invention, the surgeon builds an assembly comprising an inner electrified probe, an intermediate stent, and an outer sheath. This assembly is shown in FIG. 9. It is noted by the present inventors that if an elongated slot 51 is made in the sheath, then radially-specific neuromonitoring can be performed simply rotating the sheath. In particular, the current emanating from the probe can travel through the interstices of the mesh stent and exit through the slot, thereby producing an effectively-directional electrode that provides the operator with an indication of the proximity of nerves located just outside the slot. If the sheath is then rotated so that the slot moves to another radial location, the operator can obtain another indication of the proximity of nerves located just outside the newly-located slot.

In some directional electrode embodiments, the stent is made from an electrically-conductive nitinol (such as Nitinol-60), so that the current moves from the probe through the body of the stent and out the slot.

Therefore, in accordance with the present invention, there is provided a spinal surgery device, comprising:
 a) an electrified probe having an outer surface;
 b) a mesh stent having an inner surface and an outer surface, an unexpanded condition and an expanded condition, wherein the inner surface of the stent in its unexpanded condition contacts the outer surface of the electrified probe,
 c) an elongated sheath having a distal end, an inner surface, an outer surface and a throughhole extending from the inner surface to the outer surface of the sheath, wherein the inner surface of the sheath contacts the outer surface of the stent in its unexpanded condition.

In some embodiments, the electrified probe of the directional electrode is electrically connected to an electrical impulse generator, which is typically part of a neuromonitoring system.

In some directional electrode embodiments (FIG. 7A), the metal mesh of the stent supports a fabric 61 that prevents tissue ingress. This fabric could be electrically conductive.

In some embodiments, the elongated sheath is sized to be rotatable about the mesh, and to be slidable over the mesh.

In some directional electrode embodiments, the sheath is electrically-resistive, or comprises an electro-resistive coating thereon. This allows the directionality to be achieved.

Figure 10:
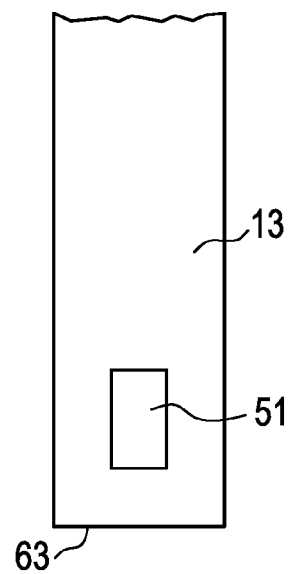
FIG. 10 discloses a side view of a sheath of a directional electrode embodiment of the assembly.

In some directional electrode embodiments (FIG. 10), the slot (or throughhole) of the sheath does not open onto the distal end 63 of the sheath. This condition allows the current to pass exclusively radially out of the slot, thereby providing directionality.

In some directional electrode embodiments, the probe does not extend past the distal end of the sheath. This condition allows the current to pass exclusively radially out of the slot, thereby providing directionality.

Figure 8:
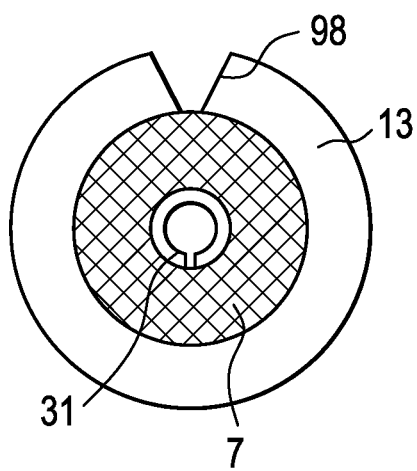
FIG. 8 is a transverse cross-section of an assembly of the present invention.

In some embodiments, the slot 98 of the sheath is tapered inward (FIG. 8).

Also in accordance with the present invention, there is provided a method of performing surgery, comprising the steps of:
 a) advancing an electrified elongated probe having an outer surface through a target tissue while performing neuromonitoring with the probe,
 b) providing an assembly comprising:
  i) an expandable mesh stent in an unexpanded condition, the stent having an outer surface and an inner surface, and
  ii) an elongated sheath having a distal end, an inner surface and a throughhole, wherein the inner surface of the sheath contacts the outer surface of the stent,
 c) sliding the assembly over the probe so that the inner surface of the stent contacts the outer surface of the probe,
 d) rotating the sheath and while performing neuromonitoring with the probe.

This method allows the surgeon to radially neuromonitor for the presence of nerves just outside the stent.

Preferably, the method further comprises the step of:
 e) withdrawing the sheath from the stent to produce an expanded stent having a bore or conduit,
 f) anchoring the stent to a bone with the probe,
 g) passing an instrument through the bore of the expanded stent, and
 h) passing an implant through the bore of the expanded stent.

Preferably, the target tissue in directional electrode embodiments is a psoas muscle having a lumbar plexus.

Figure 13:
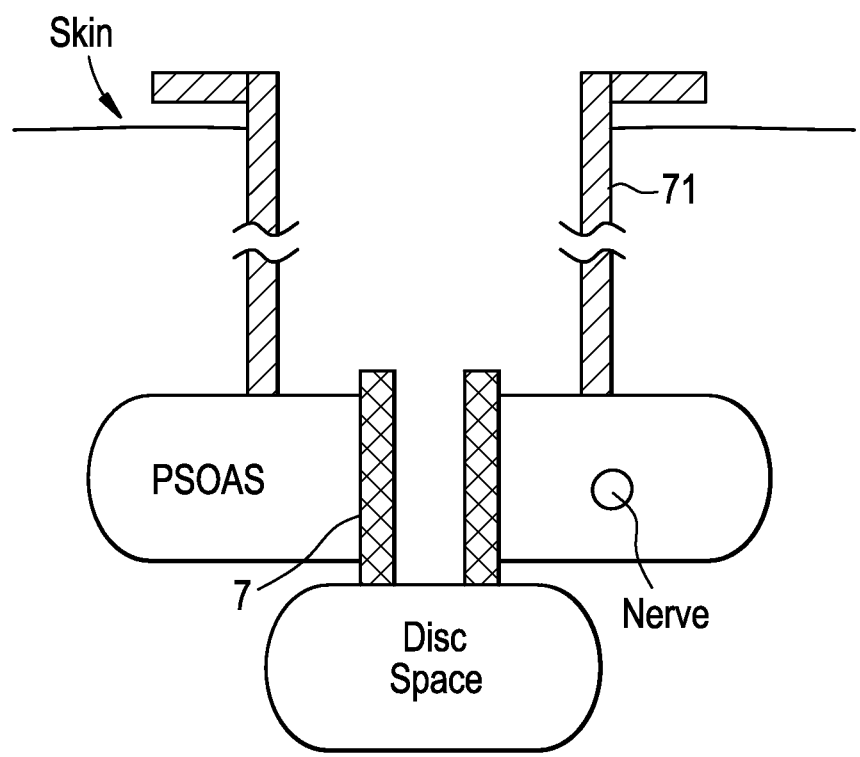
FIG. 13 shows the stent used in a shallow docking embodiment.

In some embodiments (FIG. 13), a shallow docking step is performed prior to neuromonitoring. In this case, a retractor 71 is docked in the shallow tissue proximal to the psoas and expanded. This retractor beneficially increases the visualization of the psoas. Therefore, the method may include a step, prior to neuromonitoring, of positioning a retractor proximal to the psoas muscle, and then expanding the retractor to provide an access portal for the probe.

In some embodiments, performance of the neuromonitoring results in the determination that the probe is too close to a nerve of the lumbar plexus. Therefore, in some embodiments, the method further comprises the step of:
 e) re-positioning the probe within the target tissue after performing step d).

Figure 11:
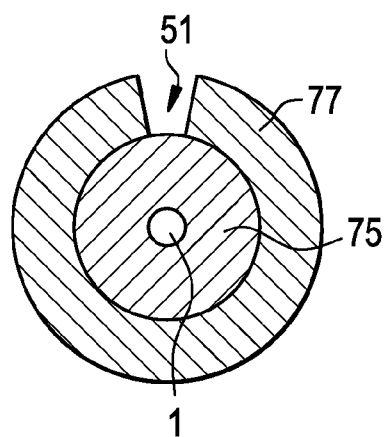
FIG. 11 discloses a transverse cross-section of a directional electrode embodiment comprising sequential dilators.

It is further noted that the concept of the directional electrode utilizing a slotted outer sheath can also be applied to sequential dilators (such as sequential concentric dilators). In such a case (FIG. 11), the initial dilator 75 that contacts the probe 1 should be made of an electrically conductive material (such as a metal), while the next dilator 77 should be made of an electrical insulator and be slotted. When this second dilator is rotated, current emanating from the initial dilator travels through the slot, thereby allowing for directional neuromonitoring.

Therefore, in accordance with the present invention, there is provided a spinal surgery device, comprising:
 a) an electrified probe having an outer surface;
 b) an electrically-conductive cannula having an inner surface and an outer surface, wherein the inner surface of the cannula contacts the outer surface of the electrified probe,
 c) an electrically-resistive elongated sheath having a distal end, an inner surface, an outer surface and a throughhole extending from the inner surface to the outer surface of the sheath, wherein the inner surface of the sheath contacts the outer surface of the cannula.

Also in accordance with the present invention, there is provided a spinal surgery device, comprising:

a) an electrified probe having an outer surface;
b) an electrically-resistive cannula having a distal end, an inner surface, an outer surface and a throughhole extending from the inner surface to the outer surface of the cannula, wherein the inner surface of the cannula contacts the outer surface of the probe.

It is further noted that the method of the present invention can be advantageously carried out without the need for sequential dilation. Therefore, in accordance with the present invention, there is provided a method of inserting an implant, comprising the steps of:
a) advancing an electrified probe through a psoas muscle,
b) advancing an expandable stent in its unexpanded condition over the electrified probe;
b) expanding the stent to its expanded condition to provide a conduit;
c) passing a spinal implant through the conduit;
d) implanting the spinal implant in an intervertebral disc space.

Preferably, this method is carried out without providing sequential dilation.

In some embodiments, the surface of the stent contains an elutable drug. The stent can have a coating containing the drug that can provide prophylactic treatments for pre-existing or iatrogenic disease. The coating can be contained within and/or elute from either the metal mesh or the fabric (if any). For instance, the coating can be an anti-inflamatory coating, such as an analgesic or an NSAID. The coating can include a drug for local anesthesia, such as lidocaine or buvacaine. The drug can be a protease inhibitor which can minimize post operative pain incurred following tissue- or psoas-retraction. The coating on the stent can be an anti-adhesive coating. The drug can be one that encourages muscle healing.

In some embodiments, the probe is eliminated and an electrode is formed on the stent. In some embodiments, this can be achieved by simply selecting an electro-conductive memory metal as a material of stent construction, and electrically connecting a proximal portion of the same stent to an electrical impulse generator. In other embodiments, this can be achieved by beginning with an electro-conductive memory metal as a material of stent construction, and then coating nearly all of the stent with an electro-resistive coating, but leaving bare a portion of the distal end portion of the stent. This bare portion will then act as a leading-end electrode for the stent that can be rotated for directional readings.

In some embodiments of the present invention, neuromonitoring for nerve proximity is performed up to the expansion of the stent. In other embodiments, neuromonitoring for nerve proximity is also performed after expansion of the stent. In some embodiments, neuromonitoring for nerve health is performed after expansion of the stent.

In some embodiments, the stent has a uniform cross-section along its length. However, in other embodiments, the stent has a non-uniform cross-section along its length. In some embodiments, the proximal end portion of the stent flares out proximally. In some embodiments, the distal end portion of the stent flares out distally. In some embodiments, the stent diameter narrows from the proximal end to the distal end, thereby allowing for ease of extraction.

In some embodiments, the stent includes a means to collapse the stent (and thereby allow for its extraction). This means is typically a suture that has been looped about the transverse cross-section of the stent. Pulling on free end of the loop reduces the diameter of the stent.

The benefits of stent retraction compared to serial dilation with mounted or hand held retractor systems include reduced incision and/or psoas dissection size, reduced bulk/weight associated with current retractors, improved radiolucency compared to current retractors, improved intraoperative flexibility as there is no rigid arm required allowing for mobility of the site, reduce pressure against the muscle/tissue as the conformable nature of stent minimizes tissue impingement forces and associated vascularity and neural restrictions problems expanded, reduced insertions compared to serial dilations, reduce time, and reduced steps.

We claim:
1. A spinal surgery device, comprising:
an electrified probe having an outer surface b) a mesh stent having an inner surface and an outer surface, an unexpanded condition and an expanded condition, wherein the inner surface of the stent in its unexpanded condition contacts the outer surface of the electrified probe,
c) an elongated sheath having a distal end, an inner surface, an outer surface and a throughhole extending from the inner surface to the outer surface of the sheath, wherein the inner surface of the sheath contacts the outer surface of the stent in its unexpanded condition.
2. The device of claim 1 wherein the electrified probe is electrically connected to an electrical impulse generator.
3. The device of claim 1 wherein the electrified probe is electrically connected to a neuromonitoring system.
4. The device of claim 1 wherein the stent has a fabric thereon for preventing tissue ingress.
5. The device of claim 4 wherein the coating is electrically conductive.
6. The device of claim 1 wherein the elongated sheath is sized to be rotatable about the mesh.
7. The device of claim 1 wherein the stent is electrically conductive.
8. The device of claim 1 wherein the sheath is electrically-resistive or has an electro-resistive coating thereon.
9. The device of claim 1 wherein the throughhole does not open onto the distal end of the sheath.
10. The device of claim 9 wherein the probe does not extend past the distal end of the sheath.
11. A method of performing surgery, comprising the steps of:
a) advancing an electrified elongated probe having an outer surface through a target tissue while performing neuromonitoring with the probe,
b) providing an assembly comprising:
i) an expandable mesh stent in an unexpanded condition, the stent having an outer surface and an inner surface, and
ii) an elongated sheath having a distal end, an inner surface and an outer surface and a throughhole extending from the inner surface to the outer surface of the elongated sheath, wherein the inner surface of the sheath contacts the outer surface of the stent,
c) sliding the assembly over the probe so that the inner surface of the stent contacts the outer surface of the probe,
d) rotating the sheath while performing neuromonitoring with the probe.
12. The method of claim 11 further comprising the step of:
e) withdrawing the sheath from the stent to produce an expanded stent having a bore.
13. The method of claim 12 further comprising the step of:
f) anchoring the stent to a bone with the probe.
14. The method of claim 12 further comprising the step of:
f) passing an implant through the bore of the expanded stent.

15. The method of claim 12 further comprising the step of:
f) passing an instrument through the bore of the expanded stent.

16. The method of claim 11 wherein the target tissue is a psoas muscle having a lumbar plexus.

17. The method of claim 16 further comprising a step before step a), comprising:
positioning a retractor proximal to the psoas muscle.

18. The method of claim 17 further comprising expanding the retractor to provide an access portal for the probe.

19. The method of claim 11 further comprising the step of:
e) re-positioning the probe within the target tissue after performing step d).

20. The method of claim 11 wherein the throughhole does not open onto the distal end of the sheath.

21. A spinal surgery device, comprising:
a) an electrified probe having an outer surface;
b) an electrically-conductive cannula having an inner surface and an outer surface, wherein the inner surface of the cannula contacts the outer surface of the electrified probe,
c) an electrically-resistive elongated sheath having a distal end, an inner surface, an outer surface and a throughhole extending from the inner surface to the outer surface of the sheath, wherein the inner surface of the sheath contacts the outer surface of the cannula.

22. The device of claim 21 wherein the electrified probe is electrically connected to an electrical impulse generator.

23. The device of claim 21 wherein the electrified probe is electrically connected to a neuromonitoring system.

24. The device of claim 21 wherein the elongated sheath is sized to be rotatable about the cannula.

25. The device of claim 21 wherein the elongated sheath is sized to be slidable over the cannula.

26. The device of claim 21 wherein the throughhole does not open onto the distal end of the sheath.

27. A spinal surgery device, comprising:
a) an electrified probe having an outer surface;
b) an electrically-resistive cannula having a distal end, an inner surface, an outer surface and a throughhole extending from the inner surface to the outer surface of the cannula, wherein the inner surface of the cannula contacts the outer surface of the probe.

28. The device of claim 27 wherein the throughhole does not open onto the distal end of the cannula.

29. The device of claim 27 wherein the electrified probe is electrically connected to an electrical impulse generator.

30. The device of claim 27 wherein the electrified probe is electrically connected to a neuromonitoring system.

31. The device of claim 27 wherein the cannula is sized to be rotatable about the probe.

32. The device of claim 27 wherein the cannula is sized to be slidable over the probe.

33. The device of claim 27 wherein the probe does not extend past the distal end of the cannula.

34. The device of claim 27 wherein the probe comprises a bare proximal end portion.

35. The device of claim 27 wherein the probe comprises a bare distal end portion.

36. The device of claim 27 wherein the distal end portion is an island.

* * * * *